United States Patent [19]

Shiao

[11] Patent Number: 5,417,683

[45] Date of Patent: May 23, 1995

[54] MINI-GRAFT HAIR IMPLANTING DEVICE FOR IMPLANTING MULTIPLE CLUMPS OF HAIR FOLLICLES AT ONE TIME

[76] Inventor: I-Shen Shiao, 1F, No.1, Alley 17, Lane 1111, Sec.2, Fu-Hsing S. Rd., Taipei City, Taiwan, Prov. of China

[21] Appl. No.: 274,455

[22] Filed: Jul. 13, 1994

[51] Int. Cl.⁶ .......................................... A61B 17/34
[52] U.S. Cl. ....................................... 606/1; 604/173
[58] Field of Search ............... 623/15; 604/48–51, 604/57, 59–64, 173, 164, 264, 117; 606/131–133, 184–189, 1

[56] References Cited

U.S. PATENT DOCUMENTS

| | | | |
|---|---|---|---|
| 4,150,669 | 4/1979 | Latorre | 604/173 |
| 4,476,864 | 10/1984 | Tezel | 606/131 |
| 4,586,490 | 5/1986 | Katz | 604/173 |

Primary Examiner—Stephen C. Pellegrino
Assistant Examiner—Glenn Dawson
Attorney, Agent, or Firm—Oblon, Spivak, McClelland, Maier & Neustadt

[57] ABSTRACT

A mini-graft hair implanting device for implanting multiple clumps of hair follicles at one time includes a barrel, a plunger and a depth control unit. The barrel is formed as a hollow cylinder with an open top and a bottom wall that has a cluster of hollow needles which are attached thereto so as to extend downwardly therefrom. Each of the hollow needles is adapted to receive a clump of hair follicles therein and has two open ends, a distal one of which is tapered so as to form a pointed tip. The plunger extends slidably into the barrel and has a bottom end that is formed with a set of downwardly extending first push rods and at least one downwardly extending second push rod. The first push rods are aligned with and extend into the hollow needles. The depth control unit is attached to and extends downwardly from the bottom wall of the barrel. The depth control unit includes at least one tube which is shorter than the hollow needles and which has two open ends, a distal one of which is blunt. Each second push rod is aligned with and extends into a corresponding tube.

5 Claims, 7 Drawing Sheets

MINI-GRAFT HAIR IMPLANTING DEVICE FOR IMPLANTING MULTIPLE CLUMPS OF HAIR FOLLICLES AT ONE TIME

BACKGROUND OF THE INVENTION

1. Field of the Invention

The invention relates to a hair implanting device, more particularly to a mini-graft hair implanting device for implanting multiple clumps of hair follicles at a single time.

2. Description of the Related Art

Currently, the most effective method for treating baldness is through hair transplants. Hair transplant is based on the following principle: It is noted that baldness usually occurs in the forehead and on the top of the head but not in the occiput and temporal regions of the head. Clinical study has proven that, by autotransplanting hair follicles or scalp from the occiput or temporal regions to the bald area on the forehead or on the top of the head, the transplanted hair can stay viable for an extended period of time.

Among the various conventional procedures for transplanting hair, "mini-graft" (1-4 hairs per clump) is considered the safest and provides the most natural and pleasing appearance. Mini-graft is also the most tedious and time-consuming procedure. Usually, this procedure initially involves the numbing of the scalp with the use of local anesthetics. A small incision is then made on the bald area of the scalp so that small clumps of hair follicles, which were obtained from the occiput region of the head, can be inserted therein with the use of a tweezer.

Although the mini-graft procedure appears to be quite simple, it is actually very difficult in real practice due to the following reasons:

1. The elasticity of the tissue surrounding the incision causes the latter to close as soon as the scalpel is pulled out, thereby obstructing the entrance of the hair follicles to be implanted and increasing the difficulty in precisely controlling the depth of hair implant.
2. Bleeding at the incision obstructs the view for inserting the hair follicles since it is difficult to pinpoint the exact location of the incision.
3. The small clump of hair follicles is very soft, thus adding to the difficulty in inserting the same into the hard-to-see incision. In unfamiliar hands, it may take minutes to implant one small clump.
4. Repeated trials may be necessary due to the difficulties in inserting the clump of hair follicles into the incision. Such repeated trials may result in damage to the hair follicles due to the use of a tweezer in implanting the same. Therefore, no hair will grow in spite of the successful implanting of the hair follicles.
5. There is a need to disinfect the equipments used in implanting the hair follicles to minimize the risk of cross-infection.

The above difficulties usually discourage many hair-implant specialists from using the mini-graft procedure.

SUMMARY OF THE INVENTION

Therefore, the object of the present invention is to provide a mini-graft hair implanting device which is capable of obviating the above drawbacks that are commonly encountered when performing the mini-graft procedure in a conventional manner.

More specifically, the object of the present invention is to provide a disposable-type mini-graft hair implanting device which is capable of implanting multiple clumps of hair at one time without the need for making a scalp incision or for using a tweezer in handling the hair follicles to be implanted.

Accordingly, the mini-graft hair implanting device of the present invention is to be used when implanting multiple clumps of hair follicles at one time and includes a barrel, a plunger, a depth control unit and a coiled compression spring unit. The barrel is formed as a hollow cylinder with an open top and a bottom wall that has a cluster of hollow needles which are attached thereto so as to extend downwardly therefrom. Each of the hollow needles is adapted to receive a clump of hair follicles therein and has two open ends, a distal one of which is tapered so as to form a pointed tip. The plunger extends slidably into the barrel and has a bottom end that is formed with a set of downwardly extending first push rods and at least one downwardly extending second push rod. The first push rods are aligned with and extend into the hollow needles. The depth control unit is attached to and extends downwardly from the bottom wall of the barrel. The depth control unit includes at least one tube which is shorter than the hollow needles and which has two open ends, a distal one of which is blunt. Each second push rod is aligned with and extends into a corresponding tube. The compression spring unit is disposed around one of the first and second push rods and is interposed between the bottom wall of the barrel and the bottom end of the plunger.

With the use of the hair implanting device of the present invention, the implanting of hair follicles is no longer manually done in a one-by-one manner. Instead, multiple (up to ten) clumps can be implanted at the same time. Furthermore, the depth of hair implant can be precisely controlled. Thus, use of the device of the present invention results in savings in time and effort. In addition, the hair implanting device can minimize damage to the hair follicles, increases viability, and by being disposable, can prevent cross-infection.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
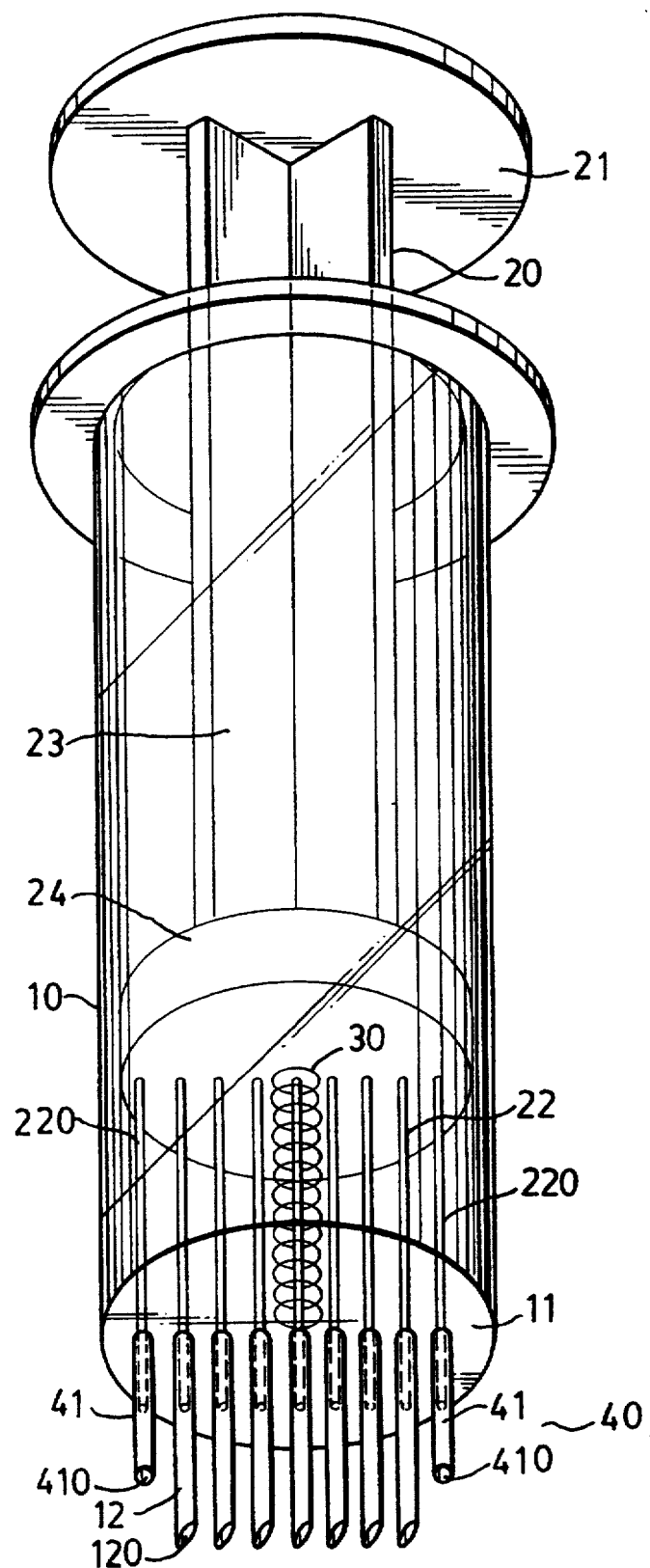
FIG. 1 is a perspective view of the first preferred embodiment of a mini-graft hair implanting device according to the present invention.

Before the present invention is described in greater detail, it should be noted that like elements are indicated by the same reference numerals throughout the disclosure.

Referring to FIG. 1, the first preferred embodiment of a mini-graft hair implanting device according to the present invention is shown to comprise a barrel 10, a plunger 20, a coiled compression spring unit 30, and a depth control unit 40.

The barrel 10 is a hollow generally elliptical cylinder with an open top and a bottom wall 11 that has a cluster (one to ten) of hollow needles 12, such as 13-16 gauge large bore needles, which are attached thereto so as to extend downwardly therefrom. In this embodiment, there are seven hollow needles 12 which are arranged in a single row and which are equal in length. Each of the hollow needles 12 has two open ends and may be made of plastic or stainless steel. The distal open end of each hollow needle 12 is tapered so as to form a pointed tip 120.

The plunger 20 includes a rod portion 23 which has a top end that is provided with a push plate 21 and a bottom end that extends into the barrel 10 and that is provided with a piston 24. The piston 24 is in sliding contact with an inner wall surface of the barrel 10 and is formed with a first set of downwardly extending push rods 22 which are aligned with and which extend into the hollow needles 12.

In this embodiment, the compression spring unit 30 is a stainless steel spring which is disposed around one of the push rods 22 and which is interposed between the bottom wall 11 of the barrel 10 and the piston 24 of the plunger 20.

The depth control unit 40 is attached to and extends downwardly from the bottom wall 11 of the barrel 10. The depth control unit 40 includes a pair of tubes 41 which are similar in construction with the hollow needles 12 except that the tubes 41 are shorter and have blunt distal open ends 410. The tubes 41 are preferably provided on two ends of the row of hollow needles 12. The piston 24 is further formed with a second set of downwardly extending push rods 220 which are aligned with and which extend into the tubes 41.

Figure 2:
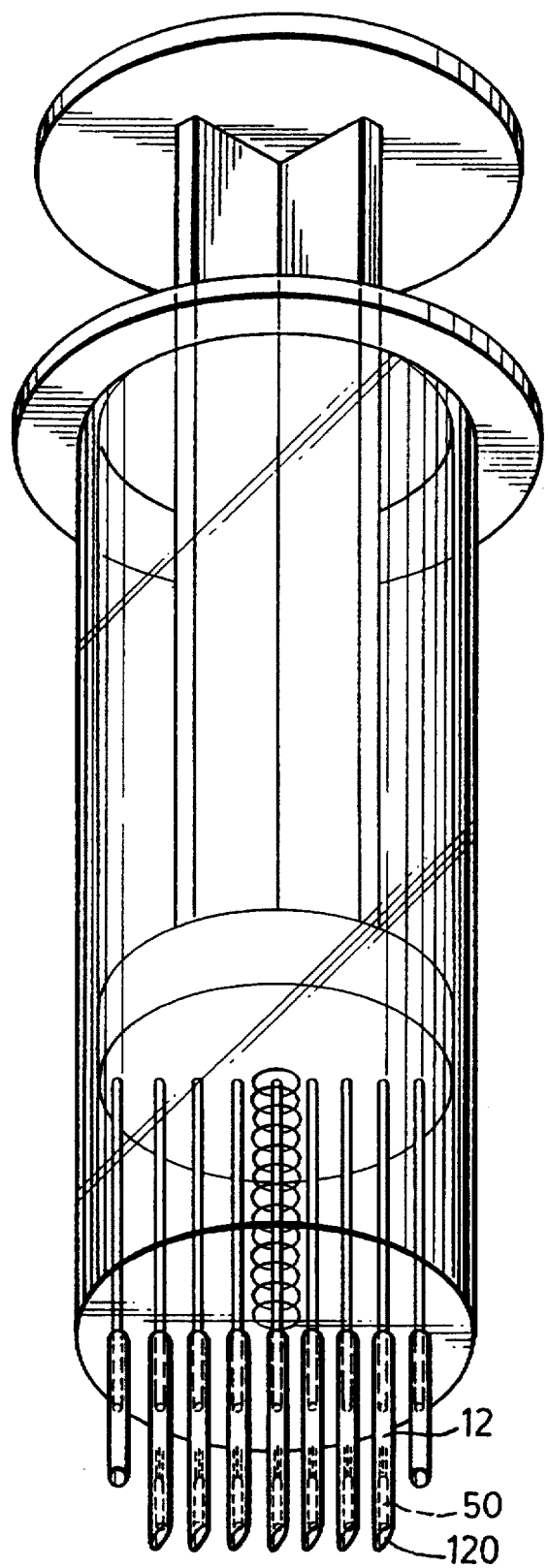
FIG. 2 is a perspective view which illustrates the first preferred embodiment when hair follicles are inserted into a cluster of hollow needles of the same.

Referring to FIG. 2, when treating a patient with the use of the mini-graft hair implanting device of the present invention, a small clump of hair follicles 50 is inserted into each of the hollow needles 12 via the respective tip 120. Preferably, each small clump includes one to four hair follicles. Since the inner diameter of the hollow needles 12 is relatively large, and since the tips 120 of the hollow needles 12 remain open and do not close, little resistance is encountered when inserting the hair follicles, thereby facilitating the mini-graft procedure. Furthermore, no blood obstructs the insertion of the hair follicles, unlike that commonly encountered when performing the conventional mini-graft procedure.

Figure 3:
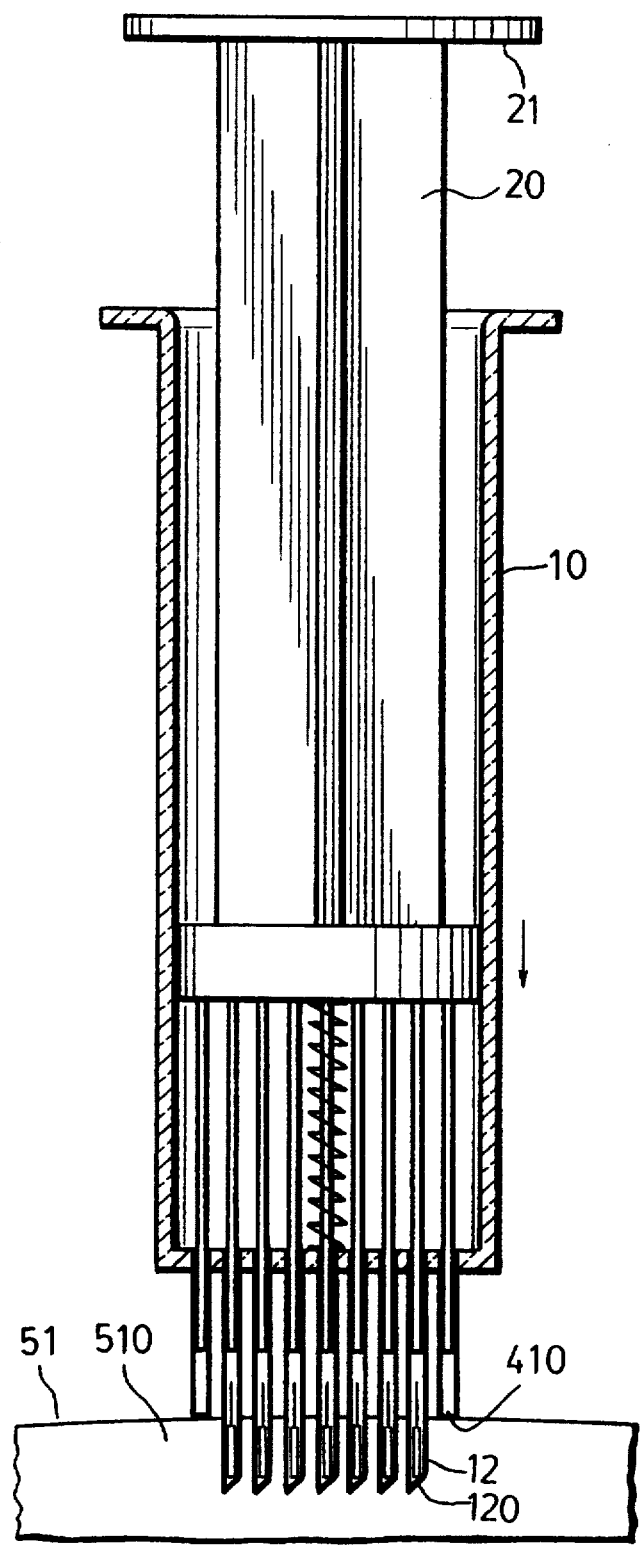
FIGS. 3 to 6 illustrate how the first preferred embodiment is used to implant hair follicles into the scalp.

Referring to FIG. 3, with one hand on the barrel 10, the surgeon positions the hair implanting device such that the hollow needles 12 are on the bald region 510 on the scalp 51 of the patient. The barrel 10 is forced toward the scalp 51 until the blunt open ends 410 of the tubes 41 of the depth control unit 40 abut the scalp 51. At this time, the tips 120 of the hollow needles 12 extend by a predetermined depth into the scalp 51.

Figure 4:
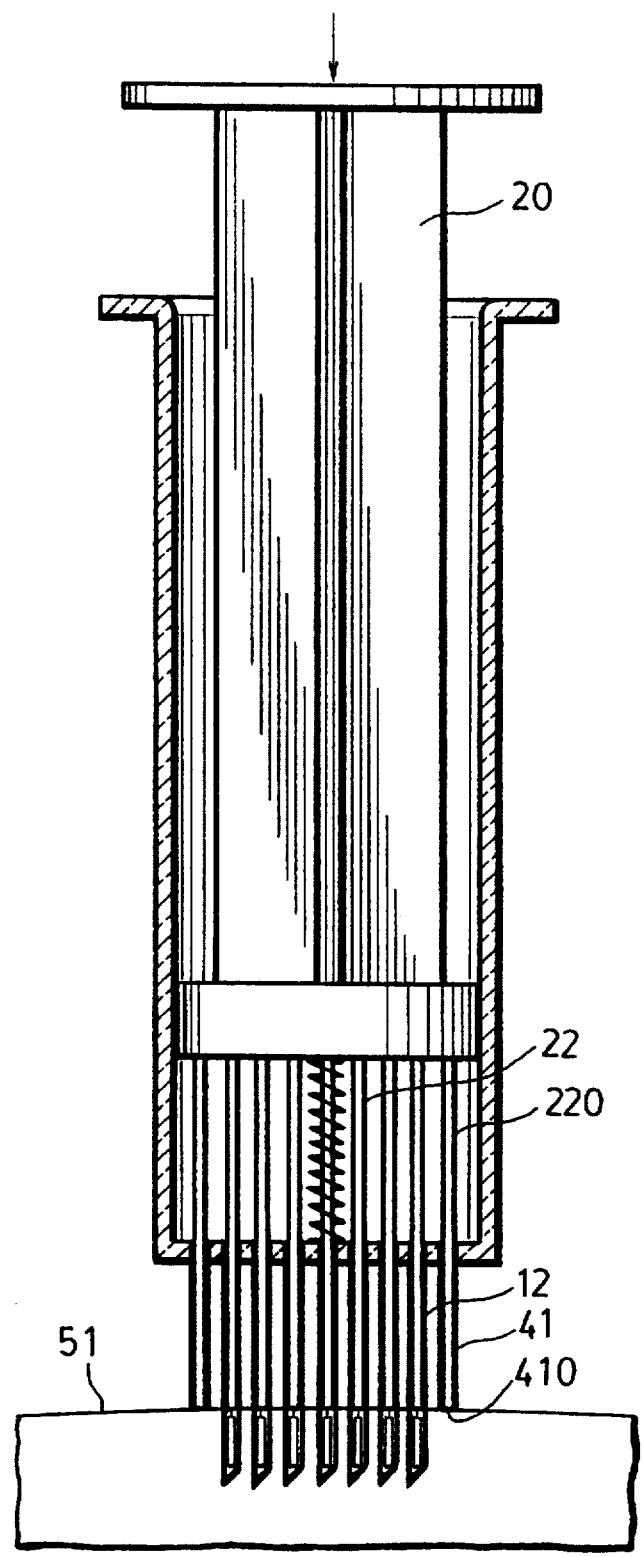

Referring to FIG. 4, the surgeon presses the plunger 20 so as to move the push rods 22, 220 in the hollow needles 12 and the tubes 41. Further movement of the push rods 22, 220 is prevented when the push rods 220 abut the scalp 51.

Figure 5:
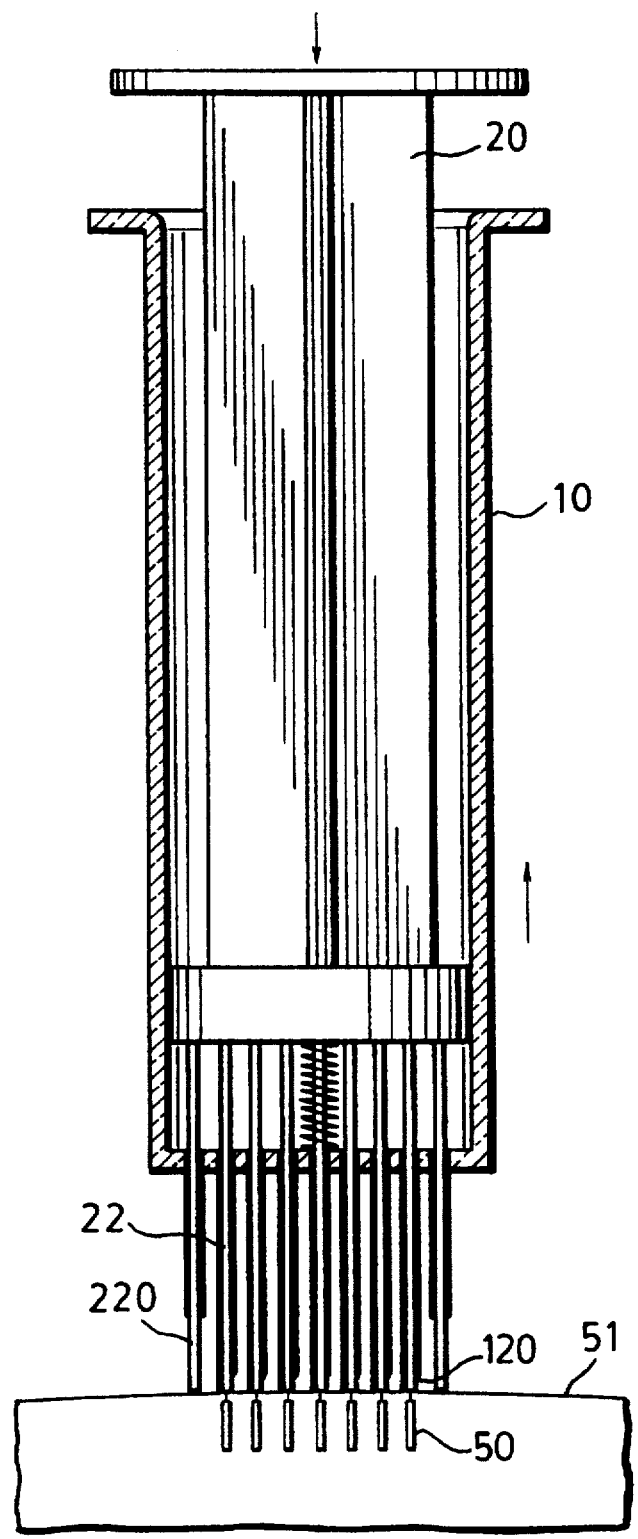

Referring to FIG. 5, the surgeon then pulls the barrel 10 away from the scalp 51, thereby withdrawing the tips 120 of the hollow needles 12 from the scalp 51. Pressure is still applied on the plunger 20 so as to force the hair follicles 50 toward the scalp 51 and prevent the hair follicles 50 from moving with the hollow needles 12, thereby retaining the hair follicles 50 on the scalp 51.

Figure 6:
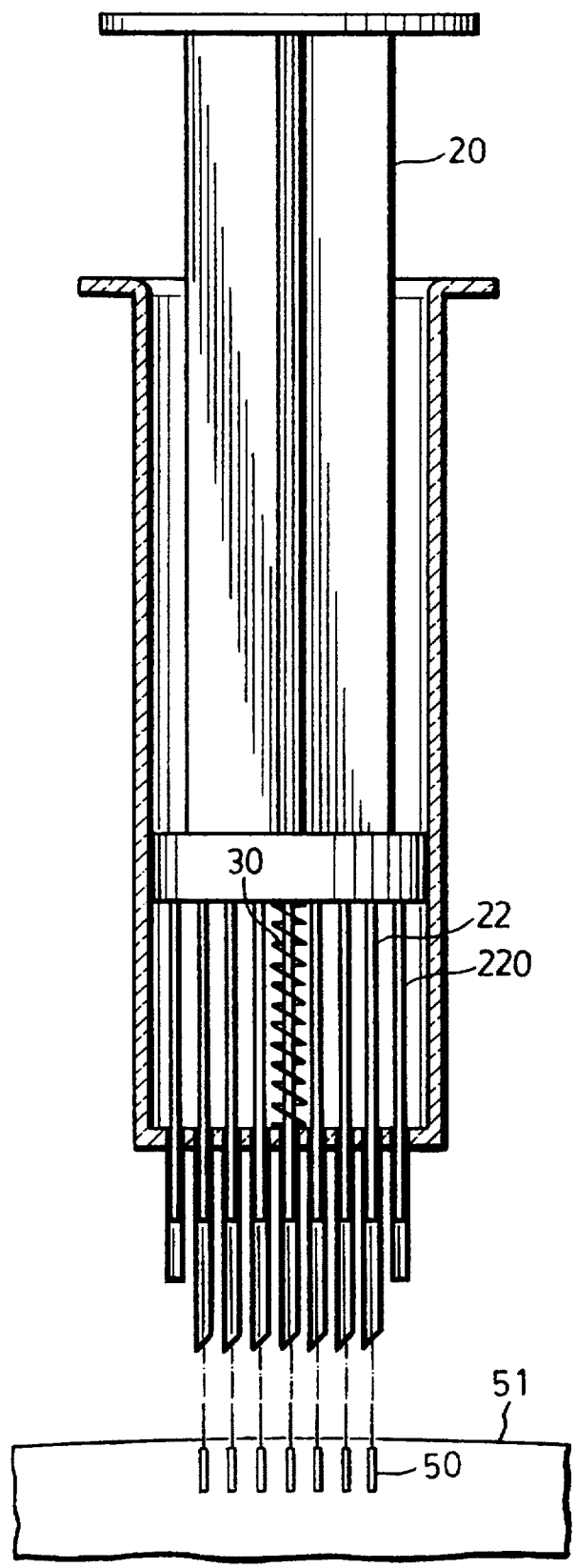

Referring to FIG. 6, when the pressure applied on the plunger 20 is extinguished, the compression spring unit 30 expands to return the push rods 22, 220 on the plunger 20 to their normal positions. The procedure for implanting the hair follicles 50 is completed at this stage. It is noted that, in this embodiment, seven small clumps of hair follicles 50 were implanted at one time.

The above procedure is performed when the hollow needles 12 are made of stainless steel. When the hollow needles 12 are made of plastic, an additional step of making incisions on the scalp prior to the implanting of hair follicles is required.

The difference in the lengths of the tubes 41 and the hollow needles 12 correspond to the desired depth of hair implant. Preferably, this difference is 7 mm, which is approximately equal to the length of a hair follicle.

Preferably, the length of each push rod 22 is approximately 1.5 cm more than the sum of the length of the hollow needles 12 and the length of the compression spring unit 30 when in a fully compressed state.

Figure 7:
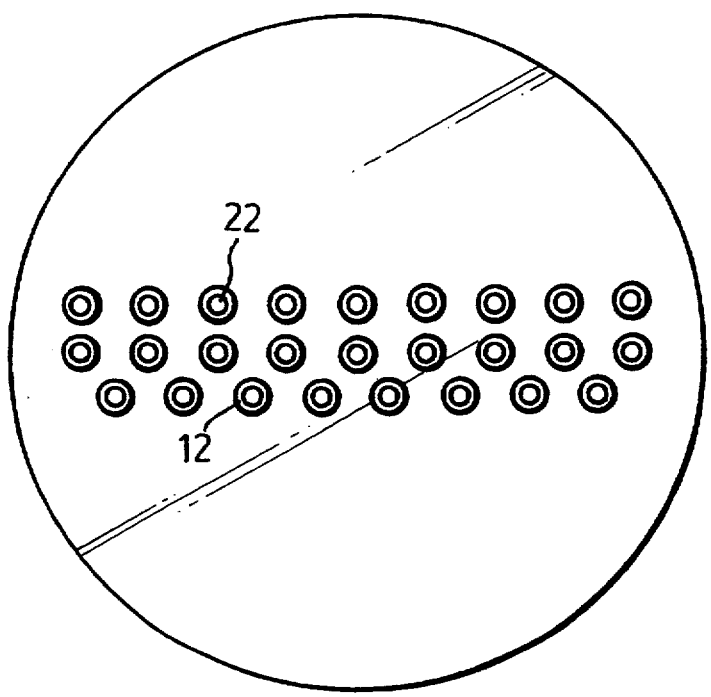
FIG. 7 is a bottom view which illustrates a barrel of the second preferred embodiment of a mini-graft hair implanting device according to the present invention.

FIG. 7 illustrates a bottom view of a barrel of the second preferred embodiment of a mini-graft hair implanting device according to the present invention. Unlike the previous embodiment, in which only one row of hollow needles 12 and push rods 22 is provided, the barrel of this embodiment is provided with several rows of hollow needles 12 and push rods 22 to permit the implanting of more clumps of hair follicles at a single time. The hollow needles 12 of adjacent rows may be aligned or staggered. The operation of the second preferred embodiment is similar to that of the previous embodiment and would not be detailed further.

Some of the advantages and characterizing features of the hair implanting device of the present invention are as follows:

1. The present invention can be used to implant one to ten small clumps of hair follicles within seconds, thereby reducing the time required to implant hair through the mini-graft procedure.
2. The depth control unit 40 permits precise control of the depth of hair implant. Furthermore, the push rods 22 can prevent the implanted hair follicles from being withdrawn from the scalp when the barrel 10 is moved away from the latter.
3. Hair follicles can be easily implanted even though bleeding occurs.
4. Hair follicles can be easily implanted even though they are very soft.
5. The use of tweezers is obviated, thereby avoiding damage to the hair follicles.
6. Cross-infection is avoided since the hair implanting device is disposable.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A mini-graft hair implanting device for implanting multiple clumps of hair follicles at one time, comprising:

a barrel formed as a hollow cylinder with an open top and a bottom wall that has a cluster of hollow needles which are attached thereto so as to extend downwardly therefrom, each of said hollow needles being adapted to receive a clump of hair follicles therein and having two open ends, a distal one of said open ends being tapered so as to form a pointed tip;

a plunger which extends slidably into said barrel and which has a bottom end that is formed with a set of downwardly extending first push rods and at least one downwardly extending second push rod, said first push rods being aligned with and extending into said hollow needles; and a depth control unit attached to and extending downwardly from said bottom wall of said barrel, said depth control unit including at least one tube which is shorter than said hollow needles and which has two open ends, a distal one of said open ends of said tube being blunt, each said second push rod being aligned with and extending into a corresponding said tube.

2. The mini-graft hair implanting device as claimed in claim 1, further comprising a coiled compression spring unit disposed around one of said first and second push rods and interposed between said bottom wall of said barrel and said bottom end of said plunger.

3. The mini-graft hair implanting device as claimed in claim 1, wherein said cluster of hollow needles includes from one to ten of said hollow needles.

4. The mini-graft hair implanting device as claimed in claim 1, wherein said tube is shorter than said hollow needles by approximately 7 mm.

5. The mini-graft hair implanting device as claimed in claim 2, wherein each of said first and second push rods has a length which is approximately 1.5 cm more than the sum of the length of one of said hollow needles and the length of said coiled compression spring unit when in a fully compressed state.

* * * * *

UNITED STATES PATENT AND TRADEMARK OFFICE
CERTIFICATE OF CORRECTION

PATENT NO. : 5,417,683
DATED : May 23, 1995
INVENTOR(S) : I-Sen SHIAO

It is certified that error appears in the above-indentified patent and that said Letters Patent is hereby corrected as shown below:

On the title page, Item [75], the inventor's name should read:

--I-Sen Shiao--

On the title page, Item [75], the inventor's address should read:

--1F, No. 1, Alley 17, Lane 111, Sec. 2, Fu-Hsing S. Rd.,
  Taipei City, Taiwan, Prov. of China--

Signed and Sealed this

Eleventh Day of July, 1995

*Attest:*

BRUCE LEHMAN

*Attesting Officer*     *Commissioner of Patents and Trademarks*